US012797580B2

(12) United States Patent
Tang

(10) Patent No.: US 12,797,580 B2
(45) Date of Patent: Nov. 17, 2026

(54) MEDICAL INSTRUMENT WITH DUAL-OUTPUT, SINGLE-INPUT DRIVE ASSEMBLY

(71) Applicant: Acclarent, Inc., Irvine, CA (US)

(72) Inventor: Raymond Yue-sing Tang, Rosemead, CA (US)

(73) Assignee: Acclarent, Inc., Irvine, CA (US)

( * ) Notice: Subject to any disclaimer, the term of this patent is extended or adjusted under 35 U.S.C. 154(b) by 71 days.

(21) Appl. No.: 18/929,812

(22) Filed: Oct. 29, 2024

(65) Prior Publication Data

US 2025/0195854 A1 Jun. 19, 2025

Related U.S. Application Data

(60) Provisional application No. 63/611,355, filed on Dec. 18, 2023.

(51) Int. Cl.
*A61M 25/01* (2006.01)
*A61M 29/02* (2006.01)

(52) U.S. Cl.
CPC ........ *A61M 25/0113* (2013.01); *A61M 29/02* (2013.01); *A61M 2205/103* (2013.01); *A61M 2210/0675* (2013.01)

(58) Field of Classification Search
CPC .............. A61M 29/02; A61M 25/0113; A61M 25/0136; A61M 2029/025
See application file for complete search history.

(56) References Cited

U.S. PATENT DOCUMENTS

| | | | |
|---|---|---|---|
| 7,720,521 B2 | 5/2010 | Chang et al. | |
| 9,155,492 B2 | 10/2015 | Jenkins et al. | |
| 9,579,448 B2 | 2/2017 | Chow et al. | |
| 10,137,285 B2 | 11/2018 | Jenkins et al. | |
| 10,206,821 B2 | 2/2019 | Campbell et al. | |
| 10,561,370 B2 | 2/2020 | Salazar et al. | |
| 11,013,896 B2 | 5/2021 | Chan et al. | |
| 11,013,897 B2 | 5/2021 | Lin et al. | |
| 11,534,192 B2 | 12/2022 | Goldfarb et al. | |
| 11,964,114 B2 | 4/2024 | Matlock et al. | |
| 2003/0191516 A1* | 10/2003 | Weldon | A61F 2/95 623/1.12 |
| 2017/0065406 A1* | 3/2017 | Calomeni | A61F 2/2436 |
| 2017/0259048 A1* | 9/2017 | Matlock | A61M 25/09041 |
| 2022/0183716 A1* | 6/2022 | Gorlewicz | A61B 17/3403 |

OTHER PUBLICATIONS

U.S. Appl. No. 63/538,093, filed Sep. 13, 2023, by Chu et al., entitled: "Balloon Dilation Instrument With Dilation Catheter Actuator."

U.S. Appl. No. 63/611,355, filed Dec 18, 2023, by Tang, entitled: "Medical Instrument With Dual-Output, Single-Input Drive Assembly."

* cited by examiner

*Primary Examiner* — Sarah A Long

(74) *Attorney, Agent, or Firm* — Morgan, Lewis & Bockius LLP

(57) ABSTRACT

An apparatus includes a body, a first guide member, a dilation catheter, a second guide member, and an actuator. The dilation catheter includes an expandable element configured to dilate an anatomical passageway within a patient. The actuator includes a rotary member operable to rotate relative to the body to thereby simultaneously drive translation of the dilation catheter along a first longitudinal range of motion and the second guide member along a second longitudinal range of motion.

21 Claims, 8 Drawing Sheets

MEDICAL INSTRUMENT WITH DUAL-OUTPUT, SINGLE-INPUT DRIVE ASSEMBLY

PRIORITY

This application claims priority to U.S. Provisional Application No. 63/611,355, entitled "Medical Instrument with Dual-Output, Single-Input Drive Assembly," filed Dec. 18, 2023, the disclosure of which is incorporated by reference herein, in its entirety.

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guidewire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pat. No. 11,534,192, entitled "Methods and Apparatus for Treating Disorders of the Sinuses," issued Dec. 27, 2022, the disclosure of which is incorporated by reference herein, in its entirety; U.S. Pat. No. 9,579,448, entitled "Balloon Dilation Catheter System for Treatment and Irrigation of the Sinuses," issued Feb. 28, 2017, the disclosure of which is incorporated by reference herein, in its entirety; U.S. Pat. No. 9,155,492, entitled "Sinus Illumination Lightwire Device," issued Oct. 13, 2015, the disclosure of which is incorporated by reference herein, in its entirety; and U.S. Pub. No. 11,964,114, entitled "Shaft Deflection Control Assembly for ENT Guide Instrument," issued Apr. 23, 2024, the disclosure of which is incorporated by reference herein, in its entirety.

In the context of Eustachian tube dilation, a dilation catheter or other dilation instrument may be inserted into the Eustachian tube and then be inflated or otherwise expanded to thereby dilate the Eustachian tube. The dilated Eustachian tube may provide improved ventilation from the nasopharynx to the middle ear and further provide improved drainage from the middle ear to the nasopharynx. Methods and devices for dilating the Eustachian tube are disclosed in U.S. Pat. No. 10,206,821, entitled "Eustachian Tube Dilation Balloon with Ventilation Path," issued Feb. 19, 2019, the disclosure of which is incorporated by reference herein, in its entirety; and U.S. Pat. No. 11,013,896, entitled "Method and System for Eustachian Tube Dilation," issued May 25, 2021, the disclosure of which is incorporated by reference herein, in its entirety.

Some medical instruments may include an adjustable guide that allows the same medical instrument to readily access different anatomical structures (e.g., Eustachian tubes and different passageways associated with drainage of paranasal sinuses, etc.). Examples of dilation instruments with adjustable guides are described in U.S. Pat. No. 10,137,285, entitled "Balloon Dilation System with Malleable Internal Guide," issued Nov. 27, 2018, the disclosure of which is incorporated by reference herein, in its entirety; U.S. Pat. No. 11,013,897, entitled "Apparatus for Bending Malleable Guide of Surgical Instrument," issued May 25, 2021, the disclosure of which is incorporated by reference herein, in its entirety; and U.S. Pat. No. 11,534,192, entitled "Methods and Apparatus for Treating Disorders of the Sinuses," issued Dec. 27, 2022, the disclosure of which is incorporated by reference herein, in its entirety.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.), such that the computer system may superimpose the current location of the instrument on the preoperatively obtained images. An example of an electromagnetic IGS navigation system that may be used in IGS procedures is the TRUDI® Navigation System by Acclarent, Inc., of Irvine, California. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, some instruments can include sensors (e.g., electromagnetic coils that emit electromagnetic fields and/or are responsive to externally generated electromagnetic fields), which can be used to perform the procedure while the sensors send data to the computer indicating the current position of each sensor-equipped instrument. The computer correlates the data it receives from the sensors with the digital map that was created from the preoperative tomographic scan. The tomographic scan images are displayed on a video monitor along with an indicator (e.g., crosshairs or an illuminated dot, etc.) showing the real-time position of each surgical instrument relative to the anatomical structures shown in the scan images. The surgeon is thus able to know the precise position of each sensor-equipped instrument by viewing the video monitor even if the surgeon is unable to directly visualize the instrument itself at its current location within the body. Examples of IGS systems that may be used in the ENT context are described in U.S. Pat. No. 7,720,521, entitled "Methods and Devices for Performing Procedures within the Ear, Nose, Throat and Paranasal Sinuses," issued May 18, 2010, the disclosure of which is incorporated by reference herein, in its entirety; and U.S. Pat. No. 10,561,370, entitled "Apparatus to Secure Field Generating Device to Chair," issued Feb. 18, 2020, the disclosure of which is incorporated by reference herein, in its entirety.

In some scenarios, it may be desirable to allow a dilation catheter of a medical instrument to translate longitudinally relative to a guide of the same instrument. This may allow the guide to be initially positioned in relation to a targeted anatomical passageway while the dilation catheter is in a proximal position. The dilation catheter may then be advanced relative to the guide to a distal position to thereby enter the targeted anatomical passageway. While several systems and methods have been made and used to dilate anatomical passageways within a patient, it is believed that no one prior to the inventors has made or used the invention described in the appended claims.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms “proximal” and “distal” are defined herein relative to a surgeon, or other operator, grasping a surgical instrument having a distal surgical end effector. The term “proximal” refers to the position of an element arranged closer to the surgeon, and the term “distal” refers to the position of an element arranged closer to the surgical end effector of the surgical instrument and further away from the surgeon. Moreover, to the extent that spatial terms such as “upper,” “lower,” “vertical,” “horizontal,” or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms “about” and “approximately” for any numerical values or ranges indicate a suitable dimensional tolerance that allows the part or collection of components to function for its intended purpose as described herein.

I. ILLUSTRATIVE DILATION INSTRUMENT WITH TRANSLATABLE DILATION CATHETER

In some scenarios, it may be desirable to advance a dilation catheter into an anatomical passageway in or near the ear, nose, or throat of a patient; and expand the dilator to thereby dilate the passageway. For instance, it may be desirable to dilate a paranasal sinus ostium or other passageway associated with drainage of a paranasal sinus cavity, a Eustachian tube, a stenotic region in an airway of a patient, etc. It may also be desirable to incorporate a guide into such an instrument, to assist in guiding the dilation catheter into the targeted anatomical passageway; and to allow the dilation catheter to translate longitudinally relative to the guide. This may allow the guide to be initially positioned in relation to a targeted anatomical passageway while the dilation catheter is in a proximal position. The dilation catheter may then be advanced relative to the guide to a distal position to thereby enter the targeted anatomical passageway.

Figure 1:
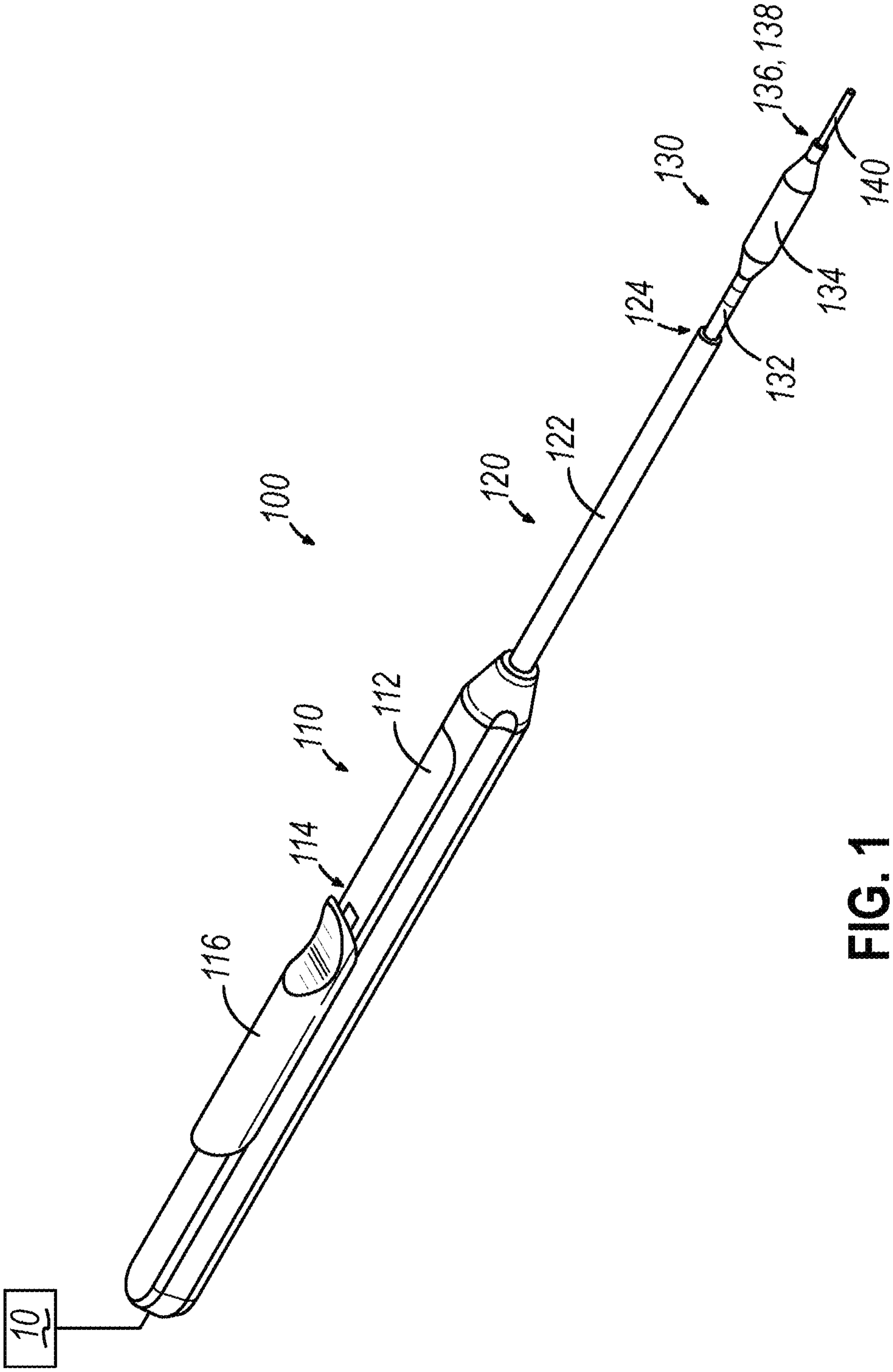
FIG. 1 depicts a perspective view of an example of a medical instrument, with a dilation catheter assembly and a guidewire in an extended position.

FIG. 1 shows an illustrative handheld dilation instrument (100). Dilation instrument (100) includes a handle assembly (110), a guide catheter (120) extending distally from handle assembly (110), a dilation catheter (130) slidably disposed within guide catheter (120), and a guidewire (140) disposed within a lumen (138) defined by dilation catheter (130). In some instances, guidewire (140) may include a light fiber, LED, or other light source that is configured to provide illumination from a distal end of guidewire (140). In addition, or in the alternative, guidewire (140) may include one or more position sensors (e.g., coils, etc.) that is/are able to provide signals (e.g., induced by an electromagnetic field) indicating a real-time position of the distal end of guidewire (140) in three-dimensional space.

Handle assembly (110) includes an elongate body (112) defining a slot (114), and an actuator (116) slidably disposed relative to elongate body (112) along a path defined by slot (114). An operator may grasp elongate body (112) with a single handle in order to control the placement of dilation instrument (100) and use a finger/thumb of the same hand in order to control the placement of actuator (116) relative to elongate body (112). In the current example, the user may translate actuator (116) longitudinally along elongate body (112). Actuator (116) is operatively attached to dilation catheter (130) such that translation of actuator (116) relative to the elongate body (112) drives translation of dilation catheter (130) relative to elongate body (112) and guide catheter (120).

Guide catheter (120) includes a shaft (122) defining a lumen that terminates into an open distal end (124). Shaft (122) is coupled to elongate body (112) and extends distally from handle assembly (110). Shaft (122) is configured to promote advancement of open distal end (124) within a suitable opening of a patient (e.g., transnasally, orally, etc.). Open distal end (124) of guide catheter (120) is dimensioned to be inserted within a patient in order to position open distal end (124) adjacent to a targeted anatomical passageway to be dilated. In some instances, a distal portion of shaft (122) near open distal end (124) may be curved/bent in order to promote suitable access to a targeted anatomical passageway to be dilated. In some instances, a distal portion of shaft (122) near open distal end (124) may be configured to selectively bend relative to the longitudinal axis of instrument (100) in order to better position open end (124) into alignment of the targeted anatomical passageway to be dilated. For instance, the distal portion of shaft (122) may be malleable, may be steerable (e.g., via one or more pull-wires, etc.), or may otherwise be selectively bent. In some other versions, the distal portion of shaft (122) includes a rigid, pre-formed bend.

In still other versions, in addition to or in lieu of providing a shaft (122) to guide dilation catheter (130) and guidewire (140) into a targeted anatomical passageway, a malleable guide rail is positioned within a dilation catheter (130), with guidewire (140) being slidably disposed within the malleable guide rail. Such an arrangement with a malleable guide rail may be provided in accordance with at least some of the teachings of U.S. Pat. No. 10,137,285, entitled "Balloon Dilation System with Malleable Internal Guide," issued Nov. 27, 2018, the disclosure of which is incorporated by reference herein, in its entirety; U.S. Pat. No. 11,013,897, entitled "Apparatus for Bending Malleable Guide of Surgical Instrument," issued May 25, 2021, the disclosure of which is incorporated by reference herein, in its entirety; and/or U.S. Pat. No. 11,534,192, entitled "Methods and Apparatus for Treating Disorders of the Sinuses," issued Dec. 27, 2022, the disclosure of which is incorporated by reference herein, in its entirety.

A lumen defined by shaft (122) is in communication with an interior of elongate body (112). As mentioned above, dilation catheter (130) is slidably disposed within guide catheter (120). Dilation catheter (130) includes an elongate shaft (132) and a dilator in the form of a balloon (134). Balloon (134) is attached to a distal end of elongate shaft (132). A proximal portion of elongate shaft (132) extends proximally past the lumen defined by shaft (122) into the interior of elongate body (112). The portion of elongate shaft (132) extending within the interior of elongate body (112) is coupled to actuator (116). Therefore, a user may actuate dilation catheter (130) relative to guide catheter (120), thereby translating dilation catheter (130) distally relative to guide catheter (120), by translating actuator (116) relative to elongate body (112).

Elongate shaft (132) defines two lumens in the current example. A first lumen of elongate shaft (132) is in fluid communication with an interior of balloon (134). The first lumen of elongate shaft (132) is also configured to selectively couple with a fluid source (10). Therefore, a user may communicate fluid (e.g., saline, etc.) from fluid source (10), through the first lumen defined by elongate shaft (132), and into the interior of balloon (134) in order to selectively expand and contract balloon (134) between an inflated and deflated configuration. A second lumen (138) defined by elongate shaft (132) extends into an open distal end (136), from which guidewire (140) extends distally.

In some instances, guidewire (140) may be affixed to open distal end (136). In other instances, guidewire (140) may be slidably disposed within lumen (138) such that guidewire (140) may translated relative to balloon catheter (130). In such instances, guidewire (140) may be attached to another actuator that may be actuated independently of actuator (116). Alternatively, a mechanism within handle assembly (110) may provide staged translation of guidewire (140) and dilation catheter (130) relative to handle assembly (112) in response to translation of actuator (116) relative to elongate body (112).

During illustrative use, balloon (134) and guidewire (140) may be housed within guide catheter (120) such that open distal end (136) of dilation catheter (130) and a distal end of guidewire (140) are each located proximally relative to open distal end (124) of guide catheter (120) (i.e., a preloaded configuration). It should be understood that while balloon (134) is in the preloaded configuration, balloon (134) may be in the deflated configuration. With dilation catheter (130) and guidewire (140) preloaded into guide catheter (120), a user may grasp handle assembly (110) in order to advance open distal end (124) of guide catheter (120) within a patient until open distal end (124) is suitably positioned near a targeted anatomical passageway.

Once open distal end (124) is suitably positioned, a user may advance actuator (116) distally relative to elongate body (112) in order to advance balloon catheter (130) distally relative to open distal end (124) such that balloon (134) is suitably disposed within the targeted anatomical passageway to be dilated. As mentioned above, in some instances, guidewire (140) may be fixed relative to balloon (134) such that guidewire (140) is advanced distally with balloon (134).

In other instances, guidewire (140) may be attached to its own actuator that may be actuated independently of actuator (116). Such a guidewire actuator may be slidably coupled to elongate body (112) of handle assembly (110). In such instances, guidewire (140) may be first advanced distally relative to open distal end (136) of dilation catheter (130) into the targeted anatomical passageway such that guidewire (140) enters the targeted anatomical passageway first, with dilation catheter (130) being subsequently advanced distally along guidewire (140) until balloon (134) is suitably positioned within the targeted anatomical passageway to be dilated. Alternatively, a mechanism within handle assembly (110) may provide staged translation of guidewire (140) and dilation catheter (130) relative to handle assembly (112) in response to translation of actuator (116) relative to elongate body (112), such that guidewire (140) is first advanced distally relative to open distal end (136) of dilation catheter (130) into the targeted anatomical passageway such that guidewire (140) enters the targeted anatomical passageway first as actuator (116) is advanced through a first range of distal motion; with dilation catheter (130) being subsequently advanced distally along guidewire (140) until balloon (134) is suitably positioned within the targeted anatomical passageway to be dilated as actuator (116) is advanced through a second range of distal motion.

In versions where the distal portion of guidewire (140) includes an illumination source (e.g., light fiber, LED, etc.), the user may observe transillumination effects through the patient's face to determine whether guidewire (140) has suitably entered a certain cavity (e.g., frontal sinus cavity, maxillary sinus cavity, etc.). In versions where the distal portion of guidewire (140) includes one or more position sensors, the user may observe a display screen of an IGS system to observe a real-time rendering of the position of the distal portion of guidewire (140) in relation to one or more preoperative images (e.g., CT scans, etc.) and/or in relation to a digital model of the patient's anatomy.

Once balloon (134) is suitably disposed within the targeted anatomical passageway, a user may inflate balloon (134) via fluid source (10) and the first lumen defined by elongate shaft (132) such that balloon (134) expands into the inflated configuration. Balloon (134) may remain in the inflated configuration until the anatomical passageway is suitably dilated. In some instances, balloon (134) may transition between the inflated and deflated configuration multiple times in order to suitably dilate the targeted anatomical passage. Once the targeted anatomical passageway is suitably dilated, a user may deflate balloon (134), proximally retract balloon (134) and guidewire (140) toward the preloaded configuration, and then remove guide catheter (120) from the patient.

II. DILATION INSTRUMENT WITH ROTARY DILATION CATHETER ACTUATOR

As noted above, it may be desirable to have a dilation instrument that incorporates an actuator to drive translation of a dilation catheter relative to a guide. Additionally, it may be desirable to have a guidewire that is also used in conjunction with a dilation catheter to further promote placement of a dilator within a targeted anatomical passageway. In some instances, guidewire (140) is slidably disposed within a lumen of dilation catheter (130) such that guidewire (140) and dilation catheter (130) each require an actuator. However, in order to simplify the advancement of dilation catheter (130) and guidewire (140) during illustrative use, it may be desirable to have a single actuator configured to advance both dilation catheter (130) and guidewire (140) in response to a single motion of the actuator.

Since guidewire (140) may be housed within lumen (138) of dilator (130) in the preloaded configuration, and also extend distally from open distal end (136) of dilator (130) when suitably placed within an anatomical passageway; guidewire (140) may be required to travel a further distance compared to dilation catheter (130). Therefore, it may be desirable to have a single actuator configured to distally translate both dilation catheter (130) and guidewire (140) in response to movement of the actuator in a single motion; but also such that the single actuator translates guidewire (140) a first distance, and simultaneously translates dilation catheter (130) a second, different distance. In other words, it may be desirable to provide advancement of guidewire (140) at a different staging or rate relative to the staging or rate of advancement of dilation catheter (130). Examples of arrangements that may be used to provide advancement of a guide element like guidewire (140) at a different staging or rate relative to the staging or rate of advancement of a dilation catheter like dilation catheter (130) are described in U.S. Provisional Pat. App. No. 63/538,093, entitled "Balloon Dilation Instrument with Dilation Catheter Actuator," filed Sep. 13, 2023, the disclosure of which is incorporated by reference herein, in its entirety.

To the extent that some conventional instruments may provide a translating actuator to drive translation of a dilation catheter and guidewire relative to a guide, some such translating actuators may provide usability difficulties. For instance, if an operator wishes to grasp the handle of the instrument with a single hand and actuate the actuator with the same hand (e.g., leaving their other hand free to manipulate an endoscope or other instrument, etc.), it may be difficult to advance the translating actuator through its full range of motion, particularly if the operator has small hands or wishes to grip the instrument in such a way that a manually driven actuator is difficult to manipulate. It may therefore be desirable to provide a dilation catheter actuator that does not require the operator to move their finger or thumb through full range of longitudinal motion to drive corresponding longitudinal motion of a dilation catheter.

To that end, it may be desirable to provide a dilation instrument that provides a rotary actuator to drive longitudinal motion of a dilation catheter and a guidewire, to facilitate driving the dilation catheter through its full range of longitudinal motion without requiring the operator to move a finger or thumb through a corresponding range of longitudinal motion.

Figure 2:
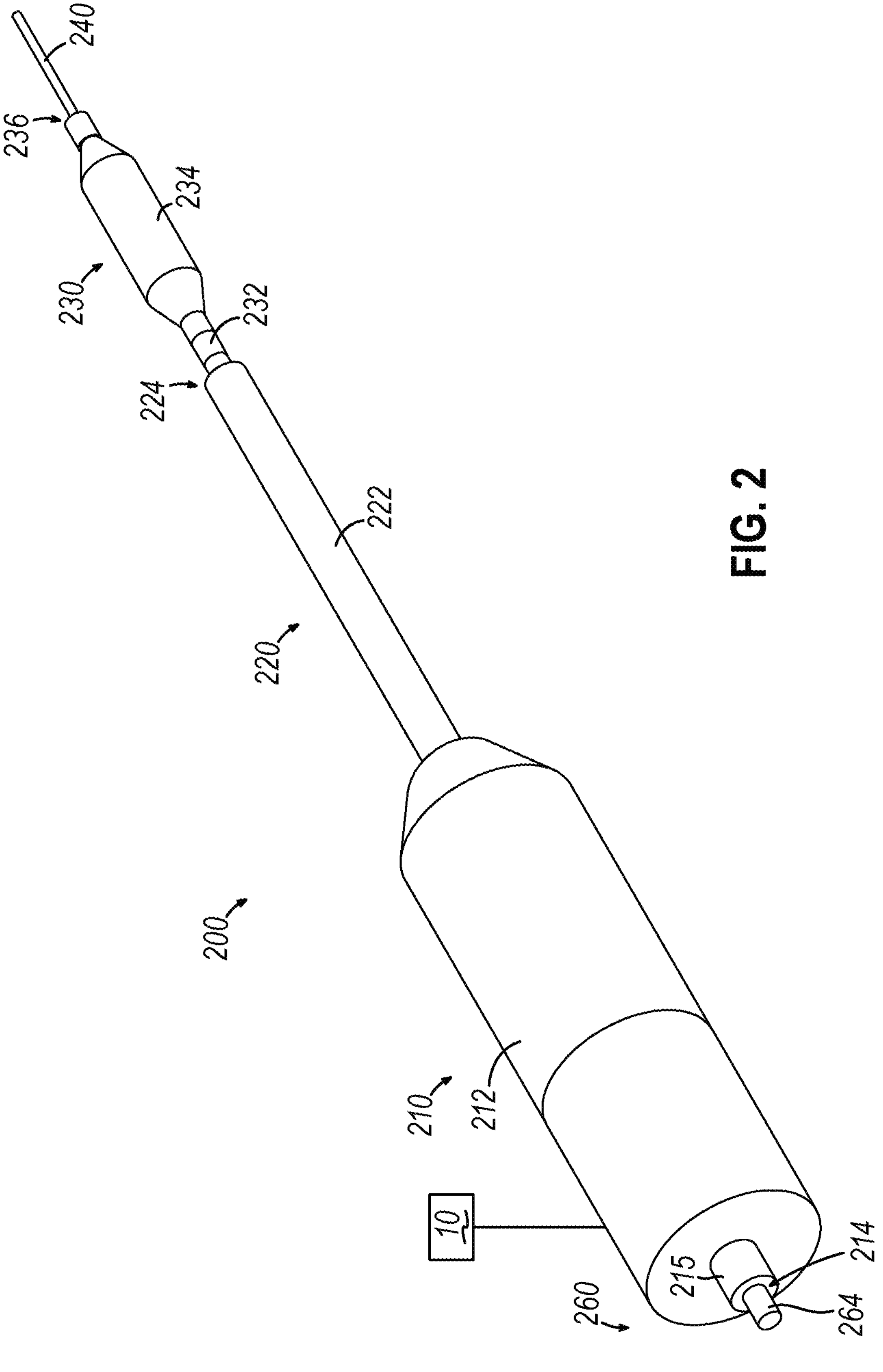
FIG. 2 depicts a perspective view of another example of a medical instrument, with a dilation catheter assembly and a guidewire in an extended position.
Figure 3:
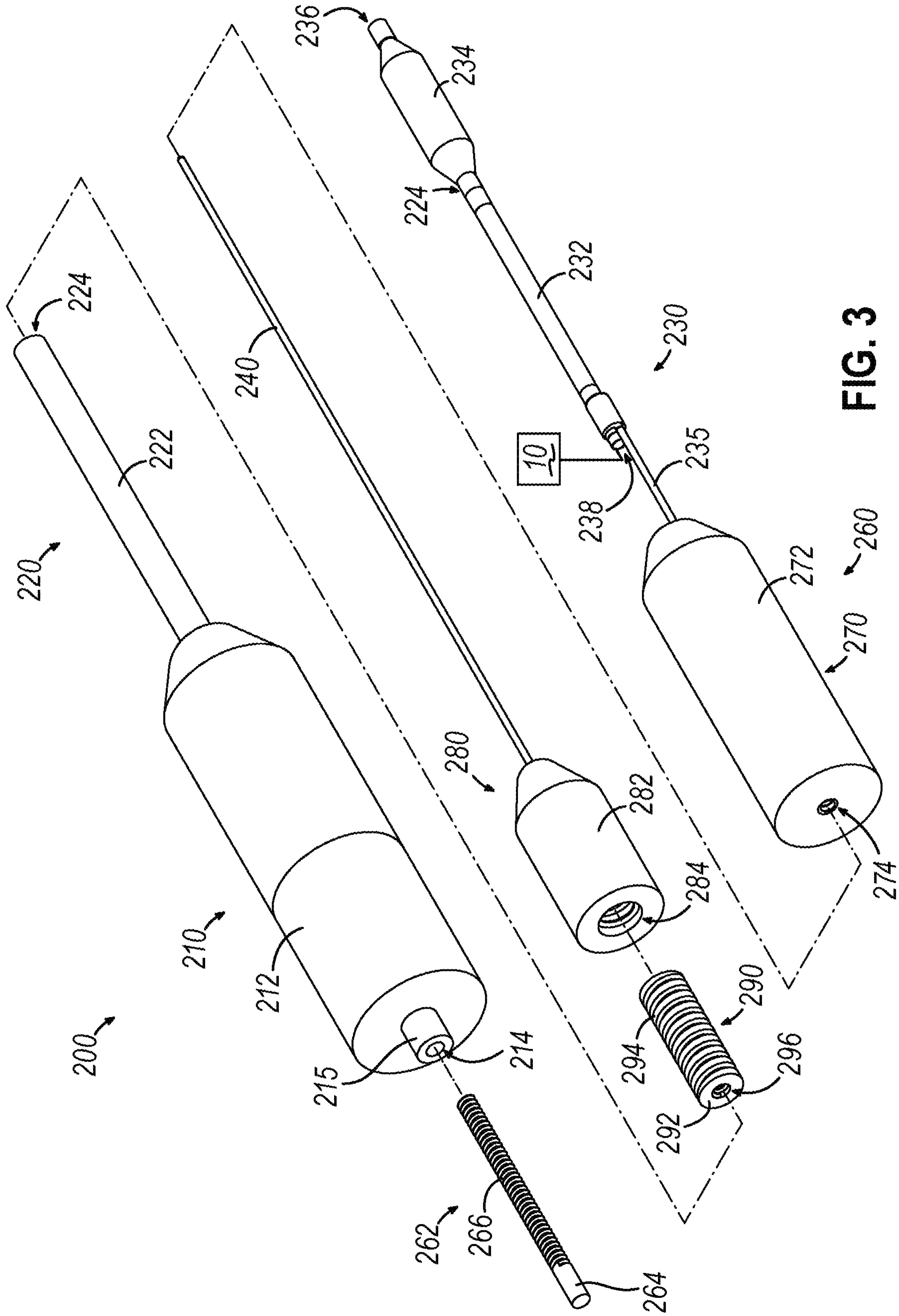
FIG. 3 depicts an exploded perspective view of the medical instrument of FIG. 2, showing an actuating assembly configured to drive the dilation catheter assembly and the guidewire of FIG. 2 between a preloaded position and an extended position.
Figure 4:
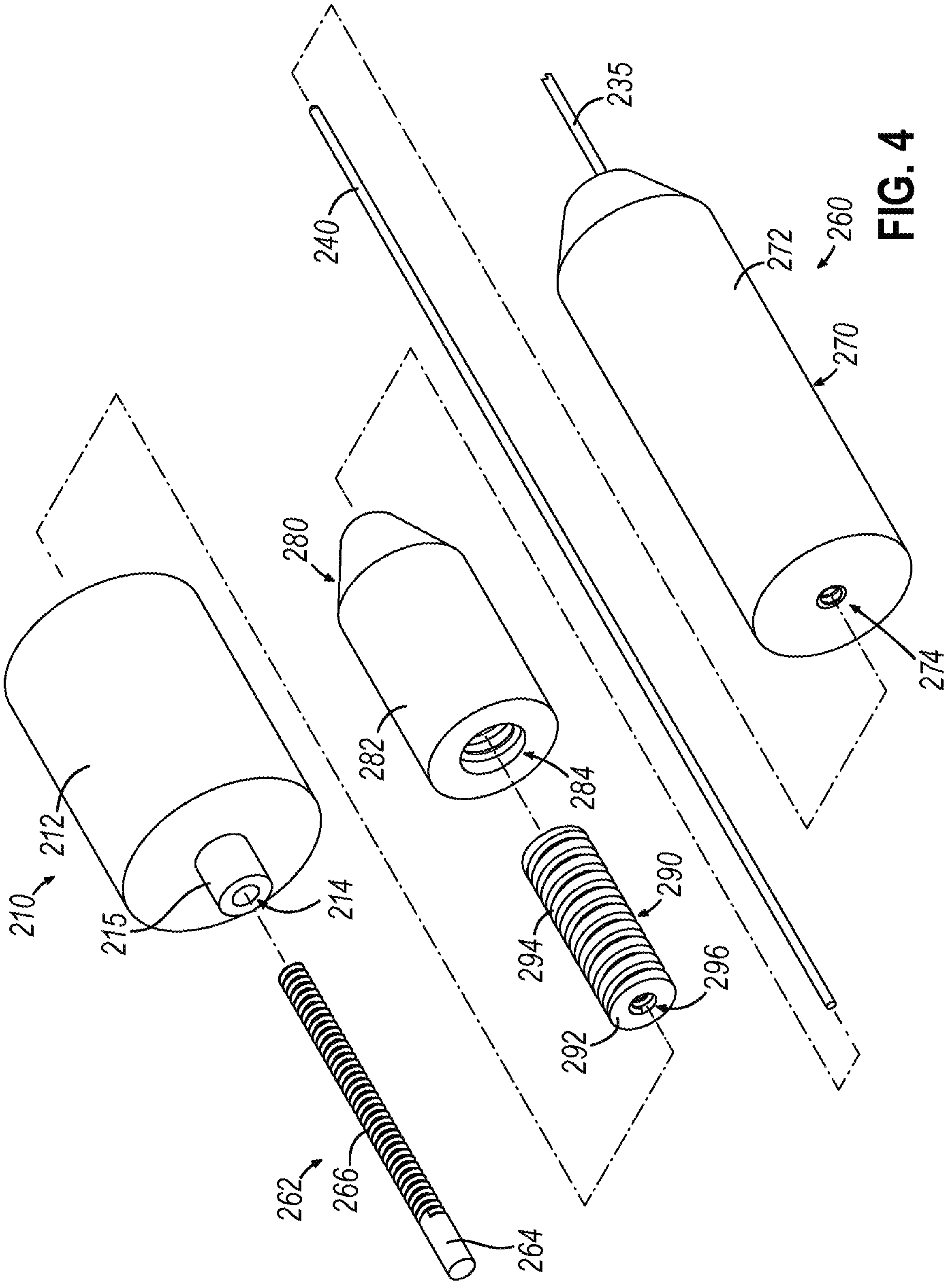
FIG. 4 depicts an exploded perspective view of the actuating assembly of FIG. 3.

FIG. 2-3 show an illustrative handheld dilation instrument (200) that may be used in replacement of handheld dilation instrument (100) described above. Therefore, handheld dilation instrument (200) includes a handle assembly (210), a guide catheter (220), a dilation catheter (230), and a guidewire (240); which may be substantially similar to handle assembly (110), guide catheter (120), dilation catheter (130), and guidewire (140) described above, respectively, with differences elaborated herein. In some instances, guidewire (240) may have an illuminating distal tip and/or one or more position sensors at or near the distal tip of guidewire (240).

Handheld dilation instrument (200) also includes an actuation assembly (260) with a single rotary input (262). As will be described in greater detail below, rotary input (262) is configured to simultaneously actuate both guidewire (240) and dilation catheter (230) in response to rotation of rotary input (262) in a single motion. As will also be described in greater detail below, rotary input (262) is configured to translate guidewire (240) a first distance while simultaneously actuating dilation catheter (230) a second distance, where the first distance traveled by guidewire (240) a further than the second distance traveled by dilation catheter (230). Therefore, rotary input (262) may rotate in a single motion to drive simultaneous actuation of both guidewire (240) and dilation catheter (230) from a preloaded configuration (see FIG. 6A) into an extended configuration (see FIG. 6C); where guidewire (240) and dilation catheter (230), while in the extended configuration, are suitably disposed within a targeted anatomical passageway (P) for purposes of dilation.

In some versions, rotary input (262) is actuated manually. By way of example only, the user may rotate rotary input (262) by directly contacting rotary input (262) with the user's hand. By way of further example only, a knob, dial, or other feature may be coupled with rotary input (262) to facilitate manual rotation of rotary input (262). In some other versions, a motor is used to provide powered rotation of rotary input (262). Alternatively, rotary input (262) may be actuated in any other suitable fashion.

Handle assembly (210) includes an elongate body (212) that may be grasped by a single hand of an operator; while guide catheter (220) includes a shaft (222) defining a lumen (228) (see FIGS. 6A-6C) terminating into an open distal end (224). Shaft (222) is coupled to elongate body (212) and extends distally from handle assembly (210). Therefore, a user may control the placement of open distal end (224), and the rest of guide catheter (220), via control of elongate body (212). Shaft (222) is configured to promote advancement of open distal end (224) within a suitable opening of a patient (e.g., transnasally, orally, etc.). Open distal end (224) of guide catheter (220) is dimensioned to be inserted within a patient in order to position open distal end (224) adjacent to a targeted anatomical passageway to be dilated. Therefore, an operator may position open distal end (224) adjacent to a targeted anatomical passageway via handle assembly (210).

Dilation catheter (230) and guidewire (240) are each slidably disposed within the lumen (228) (see FIGS. 6A-6C) of guide catheter (220). Dilation catheter (230) includes an elongate shaft (232) and a dilator in the form of a balloon (234). Elongate shaft (232) defines two lumens in the current example. A first lumen of elongate shaft (232) is in fluid communication with an interior of balloon (234). The first lumen of elongate shaft (232) is also configured to selectively couple with a fluid source (10). Therefore, a user may communicate fluid from fluid source (10), through the first lumen defined by elongate shaft (232), and into the interior of balloon (234) in order to selectively expand and contract balloon (234) between an inflated and deflated configuration.

A second lumen (238) defined by elongate shaft (232) extends into an open distal end (236). Guidewire (240) is slidably disposed within second lumen (238) of dilation catheter (230). Guidewire (240) is configured to translate from a preloaded position (see FIG. 6A), where a distal end of guidewire (240) is within second lumen (238) of dilation catheter (230), into an extended position (see FIG. 6C), where the distal end of guidewire (240) extends distally from distal end (236) of dilation catheter (230).

Shaft (222) may be malleable, steerable, or have a rigid pre-formed bend to facilitate positioning of guidewire (240) and dilation catheter (230) in a targeted anatomical passageway. In some other versions, in addition to or in lieu of providing a shaft (222) to guide dilation catheter (230) and guidewire (240) into a targeted anatomical passageway, a malleable guide rail is positioned within a dilation catheter (230), with guidewire (240) being slidably disposed within the malleable guide rail. Such an arrangement with a malleable guide rail may be provided in accordance with at least some of the teachings of U.S. Pat. No. 10,137,285, the disclosure of which is incorporated by reference herein, in its entirety; U.S. Pat. No. 11,013,897, the disclosure of which is incorporated by reference herein, in its entirety; U.S. Pat. No. 11,534,192, the disclosure of which is incorporated by reference herein, in its entirety; and/or U.S. Provisional Pat. App. No. 63/538,093, the disclosure of which is incorporated by reference herein, in its entirety.

As mentioned above, actuating assembly (260) is configured to drive translational movement of both guidewire (240) and dilation catheter (230) between their respective preloaded positions (see FIG. 6A) and their respective extended positions (see FIG. 6C) in response to rotation of rotary input (262). Actuating assembly (260) includes rotary input (262), a dilation hub (270), a guidewire hub (280), and an intermediary guidewire driver (290). As will be described in greater detail below, rotary input (262) is configured to drive translation of dilation hub (270), while rotary input (262) and intermediary guidewire driver (290) are configured to cooperatively drive translation of guidewire hub (280).

Figure 5:
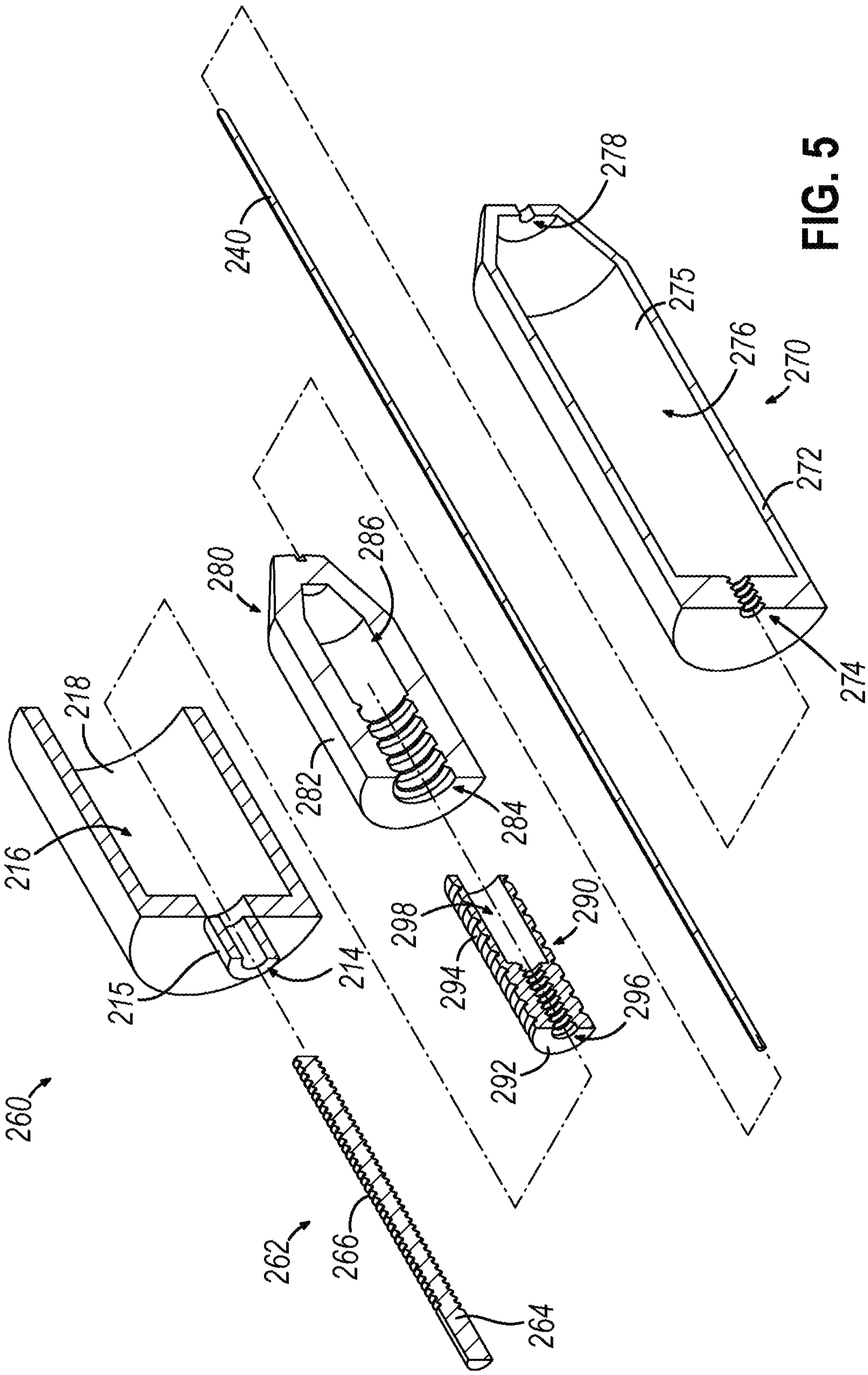
FIG. 5 depicts a sectional exploded perspective view of the actuating assembly of FIG. 3.

Rotary input (262) includes a proximal portion (264) and a distal threaded section (266). Rotary input (262) extends through a proximal through hole (214) defined by a proximal collar (215) of elongate body (212). In particular, as best shown in FIG. 2, proximal portion (264) of rotary input (262) extends proximally from collar (215). As best shown in FIGS. 5-6C, distal threaded section (266) extends within an interior cavity (216) defined by elongate body (212) of handle assembly (210). Therefore, rotary input (262) is rotatably attached to elongate body (212) of handle assembly (210).

Rotary input (262) is configured to rotate about its own longitudinal axis relative to elongate body (212). During illustrative use, a user may grasp proximal portion (264) of rotary input (262) in order to rotate rotary input (262) in a first angular direction about its longitudinal axis, or a second, opposite, angular direction about its longitudinal axis. As noted above, in some instances, proximal portion (264) includes a knob that facilitates driving rotation of rotary input (262) in accordance with the description herein. Of course, any other suitable components may be used in order to promote rotation of rotary input (262) as would be apparent to one skilled in the art in view of the teachings herein. For example, proximal portion (264) may include a worm gear operatively attached to a sliding body, where longitudinal motion of the sliding body drives rotation of the rotary input (262) via engagement between the sliding body and the worm gear.

Dilation hub (270) includes a sliding body (272) slidably disposed within interior cavity (216) defined by elongate body (212). Sliding body (272) is slidingly engaged with interior surface (218) of elongate body (212) such that sliding body (272) is configured to translate along a path defined by interior surface (218). As best shown in FIG. 3, sliding body (272) is coupled to dilation catheter (230) via an attachment rod (235). Attachment rod (235) extends from interior cavity (216) of handle assembly (210) into lumen (228) (see FIGS. 6A-6C) such that translation of sliding body (272) relative to elongate body (212) of handle assembly (210) drives corresponding translation of dilation catheter (230) relative to guide catheter (220). Therefore, sliding body (272) is configured to drive dilation catheter (230) between the preloaded position shown in FIG. 6A and the extended position shown in FIG. 6C.

Sliding body (272) of dilation hub (270) is slidably coupled to elongate body (212) of handle assembly (210) such that sliding body (272) is inhibited from rotating about its own longitudinal axis relative to elongate body (212) of handle assembly (210). Sliding body (272) may be inhibited from rotating about its own longitudinal axis relative to elongate body (212) using any suitable means as would be apparent to one skilled in the art in view of the teachings herein. For example, a longitudinally extending rib disposed on interior surface (218) of elongate body (212) and complementary longitudinally extending slot defined by an exterior of sliding body (272) may slidably couple sliding body (272) of dilation hub (270) and elongate body (212) of handle assembly (210) together. Alternatively, sliding body (272) and interior cavity (216) may include complementary rails and recesses, key and keyway features, and/or other complementary features that prevent sliding body (272) from rotating relative to elongate body (212) while still allowing sliding body (272) to translate relative to elongate body (212).

Sliding body (272) also defines a proximal threaded opening (274) extending between an exterior surface of sliding body (272) and a hollow interior (276) of sliding body (272). Distal threaded portion (266) of rotary input (262) meshes with proximal threaded opening (274) of sliding body (272). Since sliding body (272) is inhibited from rotating relative to handle assembly (210), rotation of rotary input (262) about its own longitudinal axis drives translation of sliding body (272) along the longitudinal path defined by interior surface (218) via engagement between distal threaded portion (266) and threaded opening (274). Therefore, a user may rotate rotary input (262) in a first angular direction about the longitudinal axis of rotary input (262) in order to distally translate dilation hub (270) relative to handle assembly (210). Conversely, the user may rotate rotary input (262) in a second, opposite, angular direction about the longitudinal axis of rotary input (262) in order to proximally translate dilation hub (270) relative to handle assembly (210).

It should be understood that since dilation hub (270) is coupled to dilation catheter (230), such rotation of rotary input (262) also drives translation of dilation catheter (230) relative to guide catheter (220). It should also be understood that the thread pitch (e.g., threads per inch, threads per centimeter, etc.) of threaded section (266) and threaded opening (274) determine the distance that dilation hub (270) travels in response to angular displacement of rotary input (262).

Guidewire hub (280) includes a sliding body (282) slidably disposed within hollow interior (276) of dilation hub (270). Sliding body (282) is slidingly engaged with interior surface (275) of dilation hub (270) such that sliding body (282) is configured to translate along a path defined by interior surface (275). Sliding body (282) of guidewire hub (280) is directly coupled to guidewire (240). Therefore, translation of sliding body (272) relative to dilation hub (270) and handle assembly (210) drives corresponding translation of guidewire (240) relative to dilation catheter (230) and guide catheter (220). Sliding body (282) is thus configured to drive guidewire (240) between the preloaded position shown in FIG. 6A and the extended position shown in FIG. 6C.

Sliding body (282) of guidewire hub (280) is coupled to dilation hub (270) such that sliding body (282) is inhibited from rotating about its own longitudinal axis relative to dilation hub (270). Sliding body (282) may be inhibited from rotating about its own longitudinal axis relative to dilation hub (270) using any suitable means as would be apparent to one skilled in the art in view of the teachings herein. For example, a longitudinally extending rib disposed on interior surface (275) of dilation hub (270) and a complementary longitudinally extending slot defined by an exterior of sliding body (282) may slidably couple sliding body (282) of guidewire hub (280) and dilation hub (270) together. Alternatively, sliding body (282) and interior surface (275) may include complementary rails and recesses, key and keyway features, and/or other complementary features that prevent sliding body (282) from rotating relative to dilation hub (270) while still allowing sliding body (282) to translate relative to dilation hub (270).

Sliding body (282) also defines a proximal threaded opening (284) extending between an exterior surface of sliding body (282) and a hollow interior (286) of sliding body (282). Proximal threaded opening (284) meshes with a coarse exterior threading (294) of intermediary guidewire driver (290). Coarse exterior threading (294) and proximal threaded opening (284) have a larger thread pitch compared to distal threaded section (266) of rotary input (262) and proximal threaded opening (274) of dilation hub (270). In other words, coarse exterior threading (294) and proximal threaded opening (284) have fewer threads per inch as compared to distal threaded section (266) of rotary input (262) and proximal threaded opening (274) of dilation hub (270). Since sliding body (282) is inhibited from rotating about its own longitudinal axis relative to dilation hub (270), rotation of intermediate guidewire driver (290) about its own longitudinal axis drives translation of sliding body (282) along the longitudinal path defined by dilation hub (270).

Intermediary guidewire driver (290) includes a threaded body (292) having a coarse exterior threading (294) and a fine interior threading (296) extending within a through hole (298) of threaded body (292). As mentioned above, coarse exterior threaded (294) meshes with proximal threaded opening (284) of guidewire hub (280). Additionally, through hole (298) of intermediate guidewire driver (290) receives distal threaded portion (266) of rotating input body (262) such that distal threaded portion (266) meshes with fine interior threading (296) of intermediary guidewire driver (290). Therefore, intermediary guidewire driver (290) is interposed between rotary input (262) and guidewire hub (280) via threading (266, 296, 294, 284).

Intermediary guidewire driver (290) is configured to translate relative to rotary input (262) and rotate within the hollow interior (286) of guidewire hub (280), both of which allow intermediary guidewire driver (290) to drive translation of guidewire hub (280) relative to both handle assembly (210) and dilation hub (270). In particular, in response to a user rotary input (262) in accordance with the description herein, such rotation drives translation of intermediary guidewire driver (290) via engagement between threading (266, 296). Intermediary guidewire driver (290) translates along distal threaded portion (266) of rotating input body (262) until coarse threading (294) of intermediary guidewire driver (290) abuts against internal threading (284) of guidewire hub (280) to promote sufficient braking force that inhibits further translation of intermediary guidewire driver (290) along distal threaded portion (266).

In response to no longer being able to translate along distal threaded portion (266) of rotating input body (262) via the frictional braking force imparted between coarse threaded (294) and threaded opening (284), further rotation of rotating input body (262) in turn drives concurrent rotation of intermediary guidewire driver (290). As mentioned above, guidewire hub (280) is inhibited from rotating about its own longitudinal axis. Therefore, rotation of intermediary guidewire driver (290) within hollow interior (286) of guidewire hub (280) drives longitudinal translation of guidewire hub (280) via engagement between threading (294, 284). Once the frictional braking force inhibiting translation of intermediary guidewire driver (290) relative to rotary input (262) is suitably relieved via threading (284, 294) translating guidewire hub (280) relative to intermediary guidewire driver (290), rotary input (262) may start to once again rotate relative to intermediary guidewire driver (290), thereby longitudinally translating intermediate guidewire driver (290) along the length of rotary input (262).

Guidewire hub (280) is thus translated distally and proximally via longitudinal movement of intermediary guidewire driver (290) relative to rotary input (262). Additionally, guidewire hub (280) is translated distally and proximally relative to intermediate guidewire driver (290) via rotation of coarse threading (294) within internal threading (284) of guidewire hub (280). Such movement of guidewire hub (280) translates guidewire (240) relative to both dilation catheter (230) and guide catheter (220).

It should be understood that rotation of rotation input body (262) also simultaneously drives translation of dilation hub (270) via engagement between threaded portion (264) of rotating input body (262) and proximal threaded opening (274) of dilation hub (270). The longitudinal distance that dilation hub (270) travels is dictated by the thread pitch (i.e., threads per inch) of distal threaded portion (266) and proximal threaded opening (274). Since guidewire hub (280) is driven by both rotation and translation of intermediary guidewire driver (290), and since coarse threading (294) has fewer threads per inch as compared to threaded portion (264) of rotating input body (262), guidewire hub (280) is configured to translate a further distance compared to dilation hub (270) in response to the same rotational motion of input body (262). Therefore, a user may rotate input body (262) in accordance with the description herein in order to drive translation of dilation hub (270) and dilator (230) a first distance, and simultaneously drive translation of guidewire hub (280) and guidewire (240) a second, greater distance. Such difference in travel distance allows a user to translate dilator (230) and guidewire (240) from the preloaded position (see FIG. 6A) into an extended position (FIG. 6C) in a staged fashion via a single act of continuous rotation of a single input body (262).

Figure 6A:
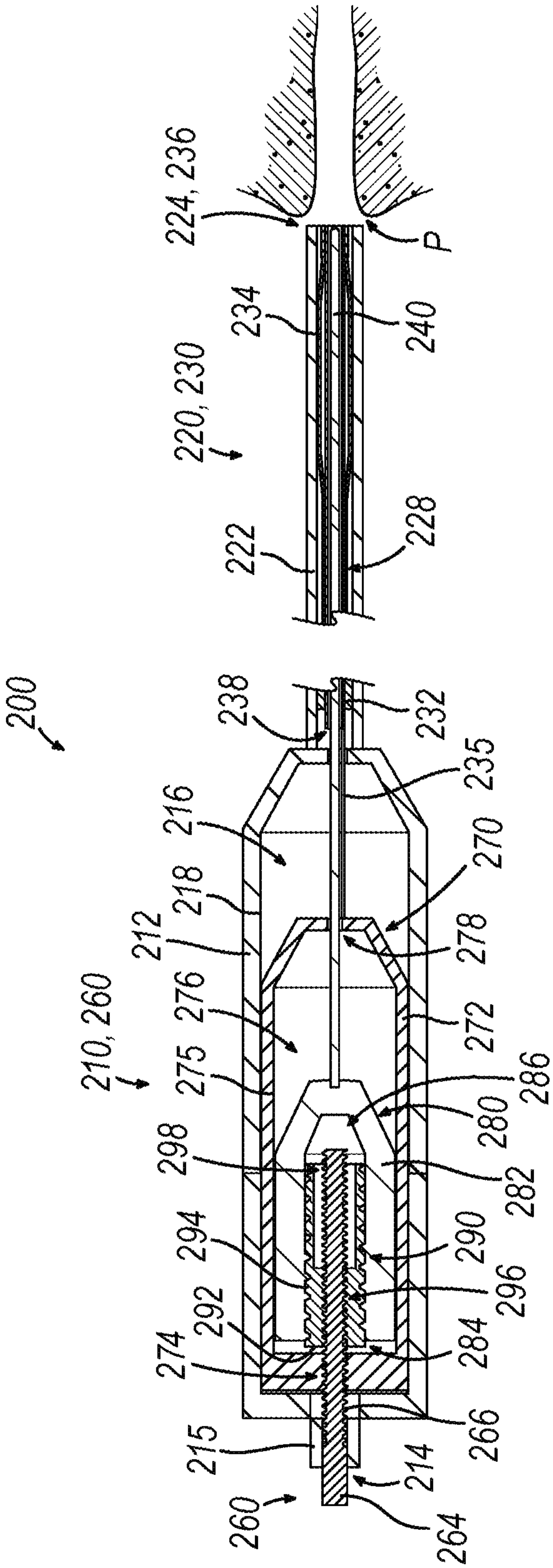
FIG. 6A depicts a cross-sectional view of the medical instrument of FIG. 2 in a preloaded position, with the balloon of the dilation catheter in a non-inflated configuration.
Figure 6B:
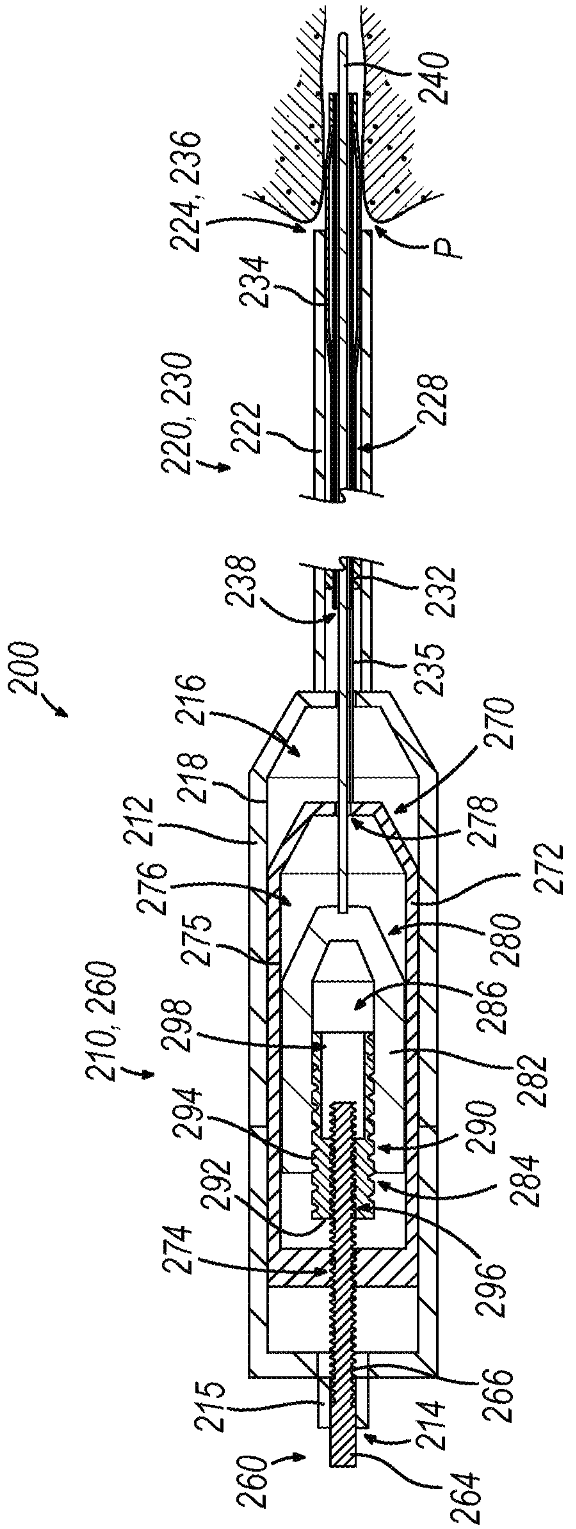
FIG. 6B depicts a cross-sectional view of the medical instrument of FIG. 2 in an intermediary position, with the balloon of the dilation catheter in the non-inflated configuration.
Figure 6C:
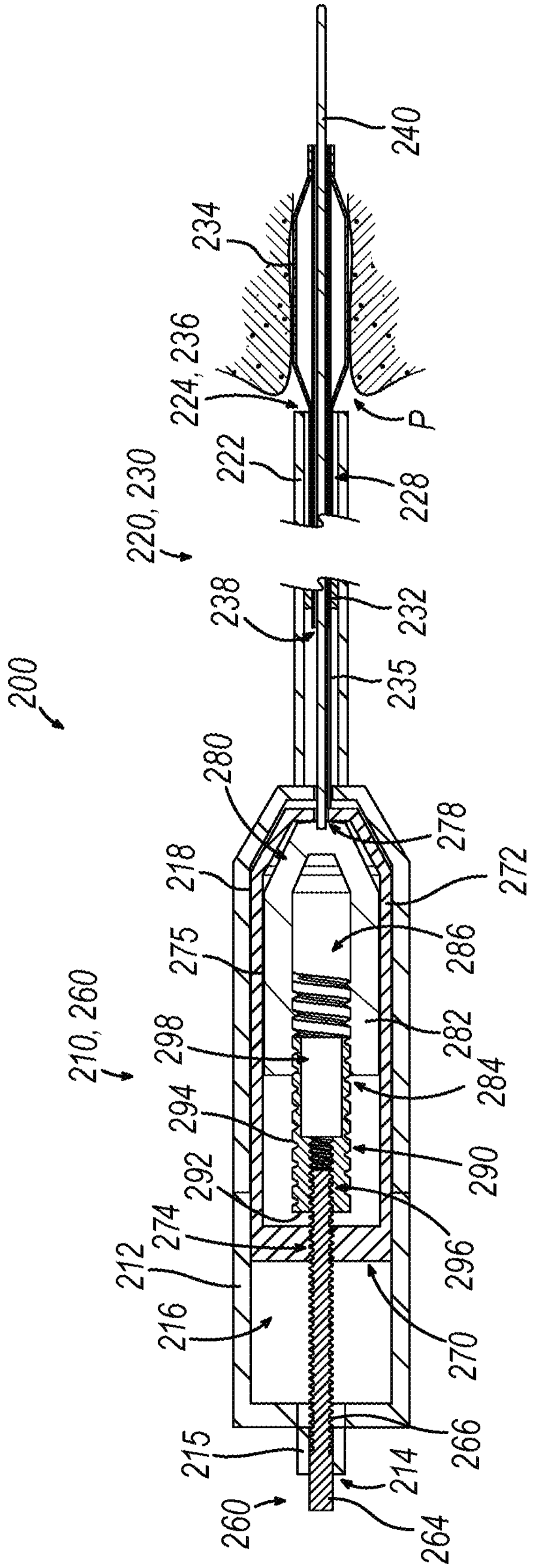
FIG. 6C depicts a cross-sectional view of the medical instrument of FIG. 2 in an extended position, with the balloon of the dilation catheter in an inflated configuration.

FIGS. 6A-6C show an illustrative use of handheld dilation instrument (200). First, as shown in FIG. 6A, with dilation catheter (230) and guidewire (240) in the preloaded position, a user may insert open distal end (224) of guide catheter (220) into a patient to thereby suitably position open distal end (224) near a targeted anatomical passageway (P). Once suitably positioned, a user may begin to rotate rotary input (262) in a first angular direction, about the longitudinal axis of rotary input (262), relative to handle assembly (210).

As shown in FIG. 6B, such initial rotation of rotary input (262) drives translation of guidewire hub (280) and guidewire (240) at a first rate of travel, while simultaneously driving translation of dilation hub (270) and dilator (230) at a second rate of travel. In particular, guidewire (240) is advanced at a greater rate of travel as compared to dilation catheter (230) in response to the same rotational movement of rotary input (262). Next, as shown in FIG. 6C, a user may further rotate rating input (262) in the first angular direction until guidewire (240) and balloon (234) are suitably housed within the targeted anatomical passageway (P). Once suitably positioned, a user may inflate balloon (234) in accordance with the description herein to dilate the targeted anatomical passageway (P). After passageway (P) is suitably dilated, the user may deflate balloon (234), and rotate rotary input (262) in a second, opposite, angular direction, about the longitudinal axis of rotary input (262) relative to handle assembly (210), to thereby proximally retract dilation catheter (230) and guidewire (240) back toward the preloaded configuration. Once suitably retracted, the user may then remove instrument (200) from the patient.

III. EXAMPLES OF COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus, comprising: (a) a body; (b) a first guide member extending distally from the body; (c) a dilation catheter slidably disposed relative to the first guide member, the dilation catheter being operable to translate relative to the body along a first longitudinal range of motion from a first proximal-most position to a first distal-most position, the dilation catheter including: (i) an expandable element configured to dilate an anatomical passageway within a patient, and (ii) a distal end; (d) a second guide member slidably disposed relative to the dilation catheter, the second guide member being operable to translate relative to the body along a second longitudinal range of motion from a second proximal-most position to a second distal-most position; and (e) an actuator, the actuator comprising a rotary member operable to rotate relative to the body to thereby simultaneously drive translation of the dilation catheter along the first longitudinal range of motion and the second guide member along the second longitudinal range of motion.

Example 2

The apparatus of Example 1, the rotary member comprising a first fine threaded section.

Example 3

The apparatus of Example 2, the actuator further comprising a dilation hub attached to the dilation catheter, the dilation hub having a second fine threaded section operatively engaged with the first fine threaded section of the rotary member.

Example 4

The apparatus of Example 3, the dilation hub comprising an attachment rod affixed to the dilation catheter.

Example 5

The apparatus of any of Examples 3 through 4, the actuator further comprising a second guide member hub attached to the second guide member, the second guide member hub comprising a first coarse threaded section.

Example 6

The apparatus of Example 5, the actuator further comprising and an intermediary second guide member driver, the intermediary second guide member driver comprising a second coarse threaded section operatively engaged with the first coarse threaded section of the second guide member hub, the intermediate second guide member driver comprising a third fine threaded section operatively engaged with the first fine threaded section.

Example 7

The apparatus of any of Examples 5 through 6, the dilation hub being slidably disposed within the body.

Example 8

The apparatus of Example 7, the second guide member hub being slidably disposed within the dilation hub.

Example 9

The apparatus of any of Examples 1 through 8, the second longitudinal range of motion being greater than the first longitudinal range of motion.

Example 10

The apparatus of any of Examples 1 through 9, the first proximal-most position being distal relative to the second proximal-most position.

Example 11

The apparatus of Example 10, the first distal-most position being proximal relative to the second distal-most position.

Example 12

The apparatus of any of Examples 1 through 11, the expandable element comprising a balloon.

Example 13

The apparatus of any of Examples 1 through 12, the rotary member comprising a proximal handle.

Example 14

The apparatus of any of Examples 1 through 13, the body comprising a proximal collar rotationally housing the rotary member.

Example 15

The apparatus of any of Examples 1 through 14, the guide member comprising a guide catheter.

Example 16

The apparatus of any of Examples 1 through 15, the body comprising a handle.

Example 17

The apparatus of any of Examples 1 through 16, the dilation catheter being positioned within an interior region of the first guide member.

Example 18

The apparatus of any of Examples 1 through 17, the first guide member comprising a hollow shaft.

Example 19

The apparatus of any of Examples 1 through 18, the first guide member having a malleable distal portion.

Example 20

The apparatus of any of Examples 1 through 19, the first guide member having a steerable distal portion.

Example 21

The apparatus of any of Examples 1 through 20, the first guide member having a rigid distal portion.

Example 22

The apparatus of Example 21, the rigid distal portion having a preformed bend.

Example 23

The apparatus of any of Examples 1 through 22, the second guide member comprising a guidewire.

Example 24

The apparatus of any of Examples 1 through 23, the second guide member including an illuminating feature at a distal end of the second guide member.

Example 25

The apparatus of any of Examples 1 through 24, the second guide member including one or more position sensors in a distal portion of the second guide member.

Example 26

An apparatus, comprising: (a) a body, the body having a first longitudinal end and a second longitudinal end, the first longitudinal end defining an opening; (b) a first guide element extending distally from the body; (c) a dilation catheter slidably disposed relative to the first guide element, the dilation catheter being operable to translate relative to the body along a first longitudinal range of motion from a first proximal-most position to a first distal-most position, the dilation catheter including: (i) an expandable element configured to dilate a passageway within a head of a patient, and (ii) a distal end; (d) a second guide element slidably disposed within the dilation catheter, the second guide element being operable to translate relative to the body along a second longitudinal range of motion from a second proximal-most position to a second distal-most position; and (e) an actuator assembly, comprising: (i) a rotary member comprising a first threaded section, the rotary member being rotatably coupled to the body, (ii) a dilation catheter hub comprising a second threaded section operatively engaged with the first threaded section of the rotary member, the dilation catheter hub being coupled to the dilation catheter, (iii) an intermediate second guide element driver comprising: (A) a third threaded section operatively engaged with the first threaded section of the rotary member, and (B) a fourth threaded section, and (iv) a second guide element hub comprising a fifth threaded section operatively engaged with the fourth threaded section of the intermediate second guide element driver, the rotary member being operable to translate the dilation catheter, the intermediate second guide element driver, and the second guide element hub in response to rotating relative to the body to thereby simultaneously translate the dilation catheter and the second guide element.

Example 27

The apparatus of Example 26, the second longitudinal range being greater than the first longitudinal range.

Example 28

The apparatus of any of Examples 26 through 27, the third threaded section having a first pitch length, the fourth threaded section having a second pitch length that is greater than the first pitch length.

Example 29

The apparatus of any of Examples 26 through 28, the dilation catheter hub being slidably housed within the body.

Example 30

An apparatus, comprising: (a) a body; (b) a guide catheter extending distally from the body; (c) a dilation catheter slidably disposed within the guide catheter, the dilation catheter being operable to translate relative to the body along a first longitudinal range of motion, the dilation catheter including: (i) an expandable element configured to dilate a passageway within a head of a patient, and (ii) a distal end; (d) a guide element slidably disposed relative to the dilation catheter, the guide element being operable to translate relative to the body along a second longitudinal range of motion; and (e) an actuator, the actuator comprising a rotary member operable to rotate relative to the body to thereby simultaneously drive translation of the dilation catheter along the first longitudinal range of motion and the guide element along the second longitudinal range of motion.

IV. MISCELLANEOUS

It should be understood that any of the teachings, expressions, embodiments, examples, etc. described herein may be combined with any of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one skilled in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. An apparatus, comprising:

(a) a body;

(b) a first guide member extending distally from the body;

(c) a dilation catheter slidably disposed relative to the first guide member, the dilation catheter being operable to translate relative to the body along a first longitudinal range of motion from a first proximal-most position to a first distal-most position, the dilation catheter including:

(i) an expandable element configured to dilate an anatomical passageway within a patient, and (ii) a distal end;

(d) a second guide member slidably disposed relative to the dilation catheter, the second guide member being operable to translate relative to the body along a second longitudinal range of motion from a second proximal-most position to a second distal-most position; and (e) an actuator, the actuator comprising a rotary member, a dilation hub, and a second guide member hub, the rotary member operable to rotate relative to the body to thereby simultaneously drive translation of the dilation catheter along the first longitudinal range of motion and the second guide member along the second longitudinal range of motion, the dilation hub slidably disposed within a first interior of the body, and the second guide member hub slidably disposed within a second interior of the dilation hub.

2. The apparatus of claim 1, the rotary member comprising a first fine threaded section.

3. The apparatus of claim 2, wherein the dilation hub is attached to the dilation catheter, the dilation hub having a second fine threaded section operatively engaged with the first fine threaded section of the rotary member.

4. The apparatus of claim 3, the dilation hub comprising an attachment rod affixed to the dilation catheter.

5. The apparatus of claim 3, wherein the second guide member hub is attached to the second guide member, the second guide member hub comprising a first coarse threaded section.

6. The apparatus of claim 5, the actuator further comprising and an intermediary second guide member driver, the intermediary second guide member driver comprising a second coarse threaded section operatively engaged with the first coarse threaded section of the second guide member hub, the intermediary second guide member driver comprising a third fine threaded section operatively engaged with the first fine threaded section.

7. The apparatus of claim 1, the second longitudinal range of motion being greater than the first longitudinal range of motion.

8. The apparatus of claim 1, the first proximal-most position being distal relative to the second proximal-most position.

9. The apparatus of claim 8, the first distal-most position being proximal relative to the second distal-most position.

10. The apparatus of claim 1, the expandable element comprising a balloon.

11. The apparatus of claim 1, the rotary member comprising a proximal handle.

12. The apparatus of claim 1, the body comprising a proximal collar rotationally housing the rotary member.

13. The apparatus of claim 1, the first guide member comprising a guide catheter.

14. The apparatus of claim 1, the body comprising a handle.

15. The apparatus of claim 1, the dilation catheter being positioned within an interior region of the first guide member.

16. The apparatus of claim 1, the first guide member comprising a hollow shaft.

17. The apparatus of claim 1, wherein the second guide member hub and the dilation hub are cylindrical and the second guide member hub is coaxial with the dilation hub.

18. The apparatus of claim 1, wherein the dilation hub is inhibited from rotating relative to the body.

19. The apparatus of claim 1, wherein the second guide member hub is inhibited from rotating relative to the body.

20. An apparatus, comprising:

(a) a body, the body having a first longitudinal end and a second longitudinal end, the first longitudinal end defining an opening;

(b) a first guide element extending distally from the body;

(c) a dilation catheter slidably disposed relative to the first guide element, the dilation catheter being operable to translate relative to the body along a first longitudinal range of motion from a first proximal-most position to a first distal-most position, the dilation catheter including:

(i) an expandable element configured to dilate a passageway within a head of a patient, and (ii) a distal end;

(d) a second guide element slidably disposed within the dilation catheter, the second guide element being operable to translate relative to the body along a second longitudinal range of motion from a second proximal-most position to a second distal-most position; and (e) an actuator assembly, comprising:

(i) a rotary member comprising a first threaded section, the rotary member being rotatably coupled to the body, (ii) a dilation catheter hub slidably disposed within a first interior of the body comprising a second threaded section operatively engaged with the first threaded section of the rotary member, the dilation catheter hub being coupled to the dilation catheter, (iii) an intermediate second guide element driver comprising:

(A) a third threaded section operatively engaged with the first threaded section of the rotary member, and (B) a fourth threaded section, and (iv) a second guide element hub slidably disposed within a second interior of the dilation catheter hub and comprising a fifth threaded section operatively engaged with the fourth threaded section of the intermediate second guide element driver, the rotary member being operable to translate the dilation catheter, the intermediate second guide element driver, and the second guide element hub in response to rotating relative to the body to thereby simultaneously translate the dilation catheter and the second guide element.

21. An apparatus, comprising:

(a) a body;

(b) a guide catheter extending distally from the body;

(c) a dilation catheter slidably disposed within the guide catheter, the dilation catheter being operable to translate relative to the body along a first longitudinal range of motion, the dilation catheter including:

(i) an expandable element configured to dilate a passageway within a head of a patient, and (ii) a distal end;

(d) a guide element slidably disposed relative to the dilation catheter, the guide element being operable to translate relative to the body along a second longitudinal range of motion; and (e) an actuator, the actuator comprising a rotary member operable to rotate relative to the body to thereby simultaneously drive translation of the dilation catheter along the first longitudinal range of motion and the guide element along the second longitudinal range of motion, a dilation hub slidably disposed within a first interior of the body, and a second guide member hub slidably disposed within a second interior of the dilation hub.

* * * * *